(12) United States Patent
Murakami et al.

(10) Patent No.: US 8,669,206 B2
(45) Date of Patent: Mar. 11, 2014

(54) COMPOSITION AND METHOD FOR CONTROLLING ARTHROPOD PESTS

(75) Inventors: Miki Murakami, Kawanishi (JP); Shigeru Saito, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/505,536

(22) PCT Filed: Nov. 18, 2010

(86) PCT No.: PCT/JP2010/071067
§ 371 (c)(1),
(2), (4) Date: Jun. 21, 2012

(87) PCT Pub. No.: WO2011/062291
PCT Pub. Date: May 26, 2011

(65) Prior Publication Data
US 2012/0277102 A1    Nov. 1, 2012

(30) Foreign Application Priority Data
Nov. 19, 2009    (JP) .................................. 2009-264265

(51) Int. Cl.
*A01N 43/56* (2006.01)
*A01N 37/30* (2006.01)
*A01P 7/04* (2006.01)

(52) U.S. Cl.
USPC ............................ 504/100; 514/341; 514/563

(58) Field of Classification Search
USPC .................................. 514/341, 563; 504/100
See application file for complete search history.

(56) References Cited

U.S. PATENT DOCUMENTS

2009/0111698 A1*    4/2009    Silverman et al. ............ 504/321
2010/0267565 A1*    10/2010    Kurahashi et al. ............ 504/322

FOREIGN PATENT DOCUMENTS

| JP | 4087942 | 2/2008 |
|---|---|---|
| JP | 2010-275202 | 12/2010 |
| WO | 2005/107468 | 11/2005 |
| WO | 2006/007595 | 1/2006 |
| WO | 2006/068669 | 6/2006 |
| WO | 2007/017433 | 2/2007 |
| WO | 2009/055044 | 4/2009 |
| WO | 2010/022251 | 2/2010 |

OTHER PUBLICATIONS

International Preliminary Report on Patentability and Written Opinion issued May 22, 2012 in International (PCT) Application No. PCT/JP2010/071067, of which the present application is the national stage.
International Search Report issued Feb. 22, 2011 in International (PCT) Application No. PCT/JP2010/071067, of which the present application is the national stage.
Written Opinion issued Feb. 22, 2011 in International (PCT) Application No. PCT/JP2010/071067, of which the present application is the national stage.
Supplementary European Search Report issued Sep. 26, 2013 in corresonding European Application No. 10 83 1681.
Itagaki et al., "Biological activities and structure-activity relationship of substitution compounds of $N$-[2-(3-indolyl)ethyl]succinamic acid and $N$-[2-(1-naphthy)ethyl]succinamic acid, derived from a new category of root-promoting substances, $N$-(phenethyl)succinamic acid analogs", Plant and Soil, vol. 255, 2003, pp. 67-75.

* cited by examiner

*Primary Examiner* — John Pak
(74) *Attorney, Agent, or Firm* — Wenderoth, Lind & Ponack, L.L.P.

(57) ABSTRACT

The present invention provides an arthropod pests control composition comprising, as active ingredients, 4-oxo-4-[(2-phenylethyl)amino]-butyric acid and a compound of formula (A); a method of controlling arthropod pests, which comprises applying effective amounts of 4-oxo-4-[(2-phenylethyl)amino]-butyric acid and a compound of formula (A) to a plant or growing site of plant; and so on.

7 Claims, No Drawings

COMPOSITION AND METHOD FOR CONTROLLING ARTHROPOD PESTS

TECHNICAL FIELD

The present invention relates to an arthropod pest control composition and an arthropod pest control method.

BACKGROUND ART

Known as an active ingredient for plant growth regulator has been 4-oxo-4-[(2-phenylethyl)amino]-butyric acid (Japanese Patent Publication No. 4,087,942).

DISCLOSURE OF INVENTION

An object of the present invention is to provide an arthropod pest control composition and an arthropod pest control method, having an excellent controlling efficacy on arthropod pests.

The present invention provides an arthropod pest control composition and an arthropod pest control method, having an excellent controlling efficacy on arthropod pests by combined use of 4-oxo-4-[(2-phenylethyl)amino]-butyric acid and a compound represented by the formula (A) below.

Specifically, the present invention includes the following [1] to [8]:

[1] An arthropod pests control composition comprising, as active ingredients, 4-oxo-4-[(2-phenylethyl)amino]-butyric acid and a compound represented by formula (A):

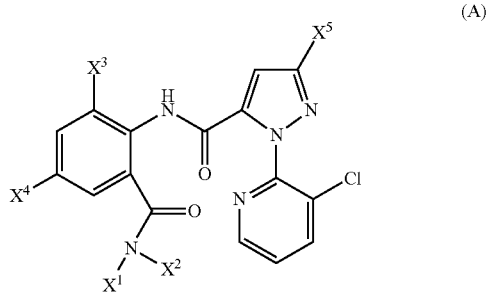

(A)

wherein $X^1$ represents a C1-C3 alkyl group or a hydrogen atom, $X^2$ represents a methyl group or —CH(CH$_3$)-cycPr, $X^3$ represents a methyl group or a halogen atom, $X^4$ represents a methyl group, a cyano group or a halogen atom, and $X^5$ represents a trifluoromethyl group or a halogen atom;

[2] The arthropod pests control composition according to [1], wherein a weight ratio of 4-oxo-4-[(2-phenylethyl)amino]-butyric acid to the compound represented by the formula (A) is in the range of 0.1:1 to 500:1;

[3] A seed treatment agent comprising, as active ingredients, 4-oxo-4-[(2-phenylethyl)amino]-butyric acid and a compound represented by formula (A) of [1];

[4] A plant seed treated with effective amounts of 4-oxo-4-[(2-phenylethyl)amino]-butyric acid and a compound represented by formula (A) of [1];

[5] A method of controlling arthropod pests which comprises applying effective amounts of 4-oxo-4-[(2-phenylethyl)amino]-butyric acid and a compound represented by formula (A) of [1] to a plant or growing site of plant;

[6] The method of controlling arthropod pests according to [5], wherein the plant is a seed or seedling;

[7] The method of controlling arthropod pests according to [5], wherein the growing site of plant is soil before or after planting the plant on it; and

[8] Combined use of 4-oxo-4-[(2-phenylethyl)amino]-butyric acid and a compound represented by formula (A) of [1] for controlling arthropod pests.

The arthropod pests control composition of the present invention has excellent control efficacy against arthropod pests.

MODE FOR CARRYING OUT THE INVENTION

The arthropod pests control composition of the present invention (hereinafter, referred to as "the composition of the present invention" in some cases) comprises, as active ingredients, 4-oxo-4-[(2-phenylethyl)amino]-4-butyric acid (hereinafter, referred to as "the compound I" in some cases) and a compound represented by the formula (A) (hereinafter, referred to as "the compound A" in some cases).

The compound 1,4-oxo-4-[(2-phenylethyl)amino]-butyric acid, is a compound described in Japanese Patent Publication No. 4,087,942 and can be produced, for example, by the method described in the publication.

The compound 1,4-oxo-4-[(2-phenylethyl)amino]-butyric acid, may be a salt with a base. Examples of the basic salt of 4-oxo-4-[(2-phenylethyl)amino]-butyric acid include the followings:

metal salts such as alkali metal salts and alkali earth metal salts (for example, salts of sodium, potassium or magnesium); salts with ammonia; and salts with organic amines such as morpholine, piperidine, pyrrolidine, mono lower alkylamine, di lower alkylamine, tri lower alkylamine, monohydroxy lower alkylamine, dihydroxy lower alkylamine and trihydroxy lower alkylamine.

Examples of substituents in the compound A include the following members.

Examples of the "C1-C3 alkyl group" represented by $X^1$ include a methyl group, an ethyl group, a propyl group and an isopropyl group.

"—CH(CH$_3$)-cycPr" represented by $X^2$ means an α-methyl-cyclopropylmethyl group.

The "halogen atom" represented by $X^3$, $X^4$ and $X^5$ means a fluorine atom, a chlorine atom, a bromine atom or an iodine atom.

Embodiments of the composition of the present invention include a composition comprising, as one of active ingredients, at least any one kind of a compound of the following compounds as the compound A:

a compound of the formula (A) in which $X^1$ is a C1-C3 alkyl group or a hydrogen atom;

a compound of the formula (A) in which $X^1$ is a methyl group, an ethyl group, a propyl group, an isopropyl group or a hydrogen atom;

a compound of the formula (A) in which $X^1$ is a hydrogen atom;

a compound of the formula (A) in which $X^2$ is a methyl group or —CH(CH$_3$)-cycPr;

a compound of the formula (A) in which $X^1$ is a hydrogen atom, and $X^2$ is a methyl group or —CH(CH$_3$)-cycPr;

a compound of the formula (A) in which $X^3$ is a methyl group or a halogen atom;

a compound of the formula (A) in which $X^3$ is a methyl group, a chlorine atom or a bromine atom;

a compound of the formula (A) in which $X^3$ is a methyl group or a bromine atom;

a compound of the formula (A) in which $X^1$ is a hydrogen atom, $X^2$ is a methyl group or —CH(CH$_3$)-cycPr, and $X^3$ is a methyl group or a bromine atom;

a compound of the formula (A) in which $X^4$ is a methyl group, a cyano group or a halogen atom;

a compound of the formula (A) in which $X^4$ is a methyl group, a cyano group, a chlorine atom or a bromine atom;

a compound of the formula (A) in which $X^4$ is a cyano group or a chlorine atom;

a compound of the formula (A) in which $X^1$ is a hydrogen atom, $X^2$ is a methyl group or —CH(CH$_3$)-cycPr, $X^3$ is a methyl group or a bromine atom, and $X^4$ is a cyano group or a chlorine atom;

a compound of the formula (A) in which $X^5$ is a trifluoromethyl group or a halogen atom;

a compound of the formula (A) in which $X^5$ is a trifluoromethyl group, a chlorine atom or a bromine atom;

a compound of the formula (A) in which $X^5$ is a bromine atom; and a compound of the formula (A) in which $X^1$ is a hydrogen atom, $X^2$ is a methyl group or —CH(CH$_3$)-cycPr, $X^3$ is a methyl group or a bromine atom, $X^4$ is a cyano group or a chlorine atom, and $X^5$ is a bromine atom.

Specific examples of the compound A include compounds (1) to (3) in which the respective substituents of $X^1$, $X^2$, $X^3$, $X^4$ and $X^5$ in the compound represented by the formula (A) are combinations described in Table 1.

TABLE 1

| Compound | $X^1$ | $X^2$ | $X^3$ | $X^4$ | $X^5$ |
|---|---|---|---|---|---|
| (1) | H | CH$_3$ | CH$_3$ | Cl | Br |
| (2) | H | CH$_3$ | CH$_3$ | CN | Br |
| (3) | H | CH(CH$_3$)-cycPr | Br | Cl | Br |

The compound (1) is chlorantraniliprole. The compound (1) is the compound described in Japanese Patent Publication No. 3,729,825 and can be produced, for example, by the method described in the publication.

The compound (2) is cyantraniliprole. The compound (2) is the compound described in International Publication No. WO 2004/067528 and can be produced, for example, by the method described in the publication.

The compound (3) is N-[2-bromo-4-chloro-6-[[α-methyl-(cyclopropylmethyl)amino]carbonyl]-phenyl]-3-bromo-1-(3-chloro-2-pyridinyl)-1H-pyrazole-5-carboxamide. The compound (3) is the compound described in Japanese Patent Publication No. 4,150,379 and can be produced, for example, by the method described in the publication.

The compound A may be a salt with an acid or a base.

Examples of the salt of the compound (1) include acid addition salts of an inorganic or organic acid such as hydrobromic acid, hydrochloric acid, nitric acid, phosphoric acid, sulfuric acid, acetic acid, butyric acid, fumaric acid, lactic acid, maleic acid, malonic acid, oxalic acid, propionic acid, salicylic acid, tartaric acid, 4-toluenesulfonic acid or valeric acid.

Examples of the salt of the compound (2) include acid addition salts of an inorganic or organic acid such as hydrobromic acid, hydrochloric acid, nitric acid, phosphoric acid, sulfuric acid, acetic acid, butyric acid, fumaric acid, lactic acid, maleic acid, malonic acid, oxalic acid, propionic acid, salicylic acid, tartaric acid, 4-toluenesulfonic acid or valeric acid.

Examples of the salt of the compound (3) include alkali metal salts such as sodium salt and potassium salt; alkali earth metal salts such as magnesium salt and calcium salt; ammonium salts such as dimethylammonium salt and triethylammonium salt; inorganic acid salts such as hydrochlorides, perchlorates, sulfates and nitrates; and organic acid salts such as acetates and methanesulfonates.

While the composition of the present invention may be a simple mixture of the compound I and the compound A, it may be prepared by mixing the compound I, the compound A and an inert carrier, and adding to the mixture a surfactant or other adjuvants as needed so that the mixture can be used as such a formulation as emulsifiable concentrate, liquid agent, microemulsion, flowable agent, oil agent, wettable powder, dust formulation, granule, microgranule, seed-coating agent, seed-soaking agent, smoking agent, tablet, microcapsule, spray, aerosol, carbon dioxide gas preparation, EW agent, capsule, pellet formulation, and trunk-coating agent. The composition of the present invention can be used as a seed treatment agent as it is or with the addition of other inert ingredients.

Examples of the solid carrier (dilution agent, extending agent) which can be used in the preparations include fine powders or granules such as plant powders (for example, soybean flour, tobacco flour, wheat flour, wood flour and so on), mineral powders (for example, clays such as kaolin clay, Fubasami clay, bentonite and acid clay, talcs such as talc powder and agalmatolite powder, silicas such as diatomaceous earth and mica powder, and so on), synthetic hydrated silicon oxide, alumina, talc, ceramic, other inorganic minerals (seriate, quartz, sulfur, active carbon, calcium carbonate, hydrated silica and so on) and chemical fertilizers (ammonium sulfate, ammonium phosphate, ammonium nitrate, urea, ammonium chloride). One or more (preferably, one or more and three or less) of these solid carriers may be mixed at suitable proportion and used.

Examples of the liquid carrier include water, alcohols (for example, methyl alcohol, ethyl alcohol, n-propyl alcohol, isopropyl alcohol, butyl alcohol, hexyl alcohol, benzyl alcohol, ethylene glycol, propylene glycol, phenoxyethanol and so on), ketones (for example, acetone, methyl ethyl ketone, methyl isobutyl ketone, cyclohexanone and so on), ethers (for example, diisopropyl ether, 1,4-dioxane, tetrahydrofuran, ethylene glycol monomethyl ether, ethylene glycol dimethyl ether, diethylene glycol monomethyl ether, propylene glycol monomethyl ether, dipropylene glycol monomethyl ether, 3-methoxy-3-methyl-1-butanol and so on), aliphatic hydrocarbons (for example, hexane, cyclohexane, kerosene, lamp oil, fuel oil, machine oil and so on), aromatic hydrocarbons (for example, toluene, xylene, ethylbenzene, dodecylbenzene, phenylxylylethane, solvent naphtha, methylnaphthalene and so on), halogenated hydrocarbons (for example, dichloromethane, trichloroethane, chloroform, carbon tetrachloride and so on), acid amides (for example, N,N-dimethylformamide, N,N-dimethylacetamide, N-methylpyrrolidone, N-octylpyrrolidone and so on), esters (for example, butyl lactate, ethyl acetate, butyl acetate, isopropyl myristate, ethyl oleate, diisopropyl adipate, diisobutyl adipate, propylene glycol monomethyl ether acetate, fatty acid glycerin ester, γ-butyrolactone and so on), nitriles (for example, acetonitrile, isobutyronitrile, propionitrile and so on), carbonates (for example, propylene carbonate and so on), and vegetable oils (for example, soybean oil, olive oil, linseed oil, coconut oil, palm oil, peanut oil, malt oil, almond oil, sesame oil, mineral oil, rosmarinic oil, geranium oil, rapeseed oil, cotton seed oil, corn oil, safflower oil, orange oil and so on). One or more (preferably; one or more and three or less) of these liquid carriers may be mixed at suitable proportion and used.

Examples of the gaseous carrier include fluorocarbon, butane gas, LPG (liquefied petroleum gas), dimethyl ether and carbon dioxide gas. These gaseous carriers can be used singly or two of them can be mixed in suitable proportion, or can be combined with a suitable liquid carrier, and used.

Examples of the surfactant include nonionic and anionic surfactants such as soaps, polyoxyethylene alkyl aryl ethers (for example, Noigen (product name, registered trademark, manufactured by Dai-Ichi Kogyo Seiyaku Co., Ltd.), EA142 (EA142(product name, manufactured by Dai-Ichi Kogyo Seiyaku Co., Ltd.), and Nonal (product name, manufactured by Toho Chemical Industry Co., Ltd.)), alkylsulfates (for example, Emal 10 (product name, registered trademark, manufactured by Kao Corporation), and Emal 40 (product name, registered trademark, manufactured by Kao Corporation)), alkylbenzene sulfonates (for example, Neogen (product name, registered trademark, manufactured by Dai-Ichi Kogyo Seiyaku Co., Ltd.), Neogen T (product name, registered trademark, manufactured by Dai-Ichi Kogyo Seiyaku Co., Ltd.), and Neopelex (product name, registered trademark, manufactured by Kao Corporation)), polyethylene glycol ethers (for example, Nonipole 85 (product name, registered trademark, manufactured by Sanyo Chemical Industries, Ltd.), Nonipole 100 (product name, registered trademark, manufactured by Sanyo Chemical Industries, Ltd.), and Nonipole 160 (product name, registered trademark, manufactured by Sanyo Chemical Industries, Ltd.)), polyoxyethylene alkyl ethers (for example, Noigen ET-135 (product name, registered trademark, manufactured by Dai-Ichi Kogyo Seiyaku Co., Ltd.)), polyoxyethylene polyoxypropylene block polymers (for example, Newpole PE-64 (product name, registered trademark, manufactured by Sanyo Chemical Industries, Ltd.)), polyhydric alcohol esters (for example, Tween 20 (product name, registered trademark, manufactured by Kao Corporation), and Tween 80 (product name, registered trademark, manufactured by Kao Corporation)), alkylsulfosuccinates (for example, Sanmorin OT20 (product name, registered trademark, manufactured by Sanyo Chemical Industries, Ltd.), and Newcalgen EX70 (product name, manufactured by TAKEMOTO Oil & Fat Co., Ltd.)), alkyl naphthalene sulfonates (for example, Newcalgen WG-1 (product name, manufactured by TAKEMOTO Oil & Fat Co., Ltd.)), and alkenyl sulfonates (for example, Sorpole 5115 (product name, registered trademark, manufactured by Toho Chemical Industry Co., Ltd.)). One or more (preferably, one or more and three or less) of these surfactants can be mixed in suitable proportion and used.

Examples of the other additives include casein, gelatin, saccharides (starch, gum arabic, cellulose derivative's, alginic acid and so on), lignin derivatives, bentonite, synthetic water-soluble polymers (polyvinyl alcohol, polyvinyl pyrrolidone, polyacrylic acids and so on), PAP (acidic isopropyl phosphate), BHT (2,6-di-tert-butyl-4-methylphenol), and BHA (mixture of 2-tert-butyl-4-methoxyphenol and 3-tert-butyl-4-methoxyphenol).

In the composition of the present invention, the weight ratio of the compound I to the compound A is typically in the range of 0.1:1 to 500:1, preferably 0.5:1 to 400:1. When the composition of the present invention is applied as a foliar spray, the weight ratio is typically in the range of 0.1:1 to 500:1, preferably 0.5:1 to 400:1. When used as a seed treatment agent, the weight ratio is typically in the range of 0.1:1 to 500:1, preferably 0.5:1 to 400:1.

In the composition of the present invention, the total amount of the compound I and the compound A (hereinafter referred to as the amount of the active ingredients) is typically within a range from 0.01 to 95% by weight, preferably from 0.1 to 80% by weight, and more preferably from 1 to 50% by weight. When the composition of the present invention is prepared into emulsifiable concentrate, liquid agent or wettable powder such as granulated wettable powder, the amount of the active ingredients is typically within a range from 1 to 90% by weight, preferably from 1 to 80% by weight, and more preferably from 5 to 60% by weight. When the composition of the present invention is prepared into oil agent or dust formulation, the amount of the active ingredients is typically within a range from 0.01 to 90% by weight, preferably from 0.1 to 50% by weight, and more preferably from 0.1 to 20% by weight. When the composition of the present invention is prepared into granule, the amount of the active ingredients is typically within a range from 0.1 to 50% by weight, preferably from 0.5 to 50% by weight, and more preferably from 1 to 20% by weight.

In the composition of the present invention, the content of a liquid carrier or a solid carrier is, for example, within a range from 1 to 90% by weight, and preferably from 1 to 70% by weight, and the content of a surfactant is, for example, within a range from 1 to 20% by weight, and preferably from 1 to 15% by weight. When the composition of the present invention is prepared into liquid agent, the content of water is, for example, from 20 to 90% by weight and the content of the surfactant is from 1 to 20% by weight, and preferably from 1 to 10% by weight.

The composition of the present invention can protect plants from damages by arthropod pests which cause damages such as feeding and sucking to plants. Examples of arthropod pests against which the composition of the present invention has control efficacy include the following harmful insects and harmful mites.

Hemiptera: planthoppers such as small brown planthopper (*Laodelphax striatellus*), brown rice planthopper (*Nilaparvata lugens*) and white-backed rice planthopper (*Sogatella furcifera*); leafhoppers such as green rice leafhopper (*Nephotettix cincticeps*) and green rice leafhopper (*Nephotettix virescens*); aphids such as cotton aphid (*Aphis gossypii*), green peach aphid (*Myzus persicae*), cabbage aphid (*Brevicoryne brassicae*), potato aphid (*Macrosiphum euphorbiae*), foxglove aphid (*Aulacorthum solani*), oat bird-cherry aphid (*Rhopalosiphum padi*) and tropical citrus aphid (*Toxoptera citricidus*); stink bugs such as green stink bug (*Nezara antennata*), bean bug (*Riptortus clavetus*), rice bug (*Leptocorisa chinensis*), white spotted spined bug (*Eysarcoris parvus*), brown marmorated stink bug (*Halyomorpha mista*) and tarnished plant bug (*Lygus lineolaris*); whiteflies such as greenhouse whitefly (*Trialeurodes vaporariorum*), sweetpotato whitefly (*Bemisia tabaci*) and silverleaf whitefly (*Bemisia argentifolii*); scales such as california red scale (*Aonidiella aurantii*), san Jose scale (*Comstockaspis perniciosa*), citrus snow scale (*Unaspis citri*), red wax scale (*Ceroplastes rubens*) and cottony cushion scale (*Icerya purchasi*); lace bugs; and psyllids;

Lepidoptera: pyralid moths such as rice stem borer (*Chilo suppressalis*), yellow stem borer (*Tryporyza incertulas*), rice leafroller (*Cnaphalocrocis medinalis*), cotton leafroller (*Notarcha derogata*), indian meal moth (*Plodia interpunctella*), oriental corn borer (*Ostrinia furnacalis*), european corn borer (*Ostrinia nubilaris*), cabbage webworm (*Hellula undalis*) and bluegrass webworm (*Pediasia teterrellus*); owlet moths such as common cutworm (*Spodoptera litura*), beet armyworm (*Spodoptera exigua*), rice armyworm (*Pseudaletia separata*), cabbage armyworm (*Mamestra brassicae*), black cutworm (*Agrotis ipsilon*), beet semi-looper (*Plusia nigrisigna*), *Thoricoplusia* spp., *Heliothis* spp., and *Helicoverpa* spp.; Pieridae such as cabbage butterfly (*Pieris rapae*); tortricid moths such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana fasciata*), smaller tea tortrix (*Adoxophyes* sp.), oriental tea tortrix (*Homona magnanima*), apple tortrix (*Archips fuscocupreanus*), and codling moth (*Cydia pomonella*); leafblotch miners such as tea leafroller (*Caloptilia theivora*), and apple leafminer (*Phyllonorycter ringoneella*); fruitworm moths such as peach fruit moth (*Carposina niponensis*); lyonetiid moths such as *Lyonetia* spp.; tussock moths such as *Lymantria* spp., and *Euproctis* spp.; yponomeutid moths such as diamondback moths (*Plutella xylostella*); gelechiid moths such as pink bollworm (*Pectinophora gossypiella*), and potato tubeworm (*Phthorimaea operculella*); tiger moths such as fall webworm (*Hyphantria cunea*); and tineid moths such as casemaking clothes moth (*Tinea translucens*), and webbing clothes moth (*Tineola bisselliella*);

Thysanoptera: thrips (Thripidae) such as yellow citrus thrip (*Frankliniella occidentalis*), melon thrip (*Thrips parmi*), yellow tea thrip (*Scirtothrips dorsalis*), onion thrip (*Thrips tabaci*), flower thrip (*Frankliniella intonsa*), and tobacco thrip (*Frankliniella fusca*);

Diptera: house fly (*Musca domestica*); common house mosquito (*Culex pipiens pallens*); common horse fly (*Tabanus trigonus*); onion maggot (*Hylemya antiqua*); seedcorn maggot (*Hylemya platura*); hyrcanus group mosquito (*Anopheles sinensis*); leaf miners such as rice leafminer (*Agromyza oryzae*), rice leafminer (*Hydrellia griseola*), rice stem maggot (*Chlorops oryzae*) and legume leafminer (*Liriomyza trifolii*); melon fly (*Dacus cucurbitae*); and Mediterranean fruit fly (*Ceratitis capitata*);

Coleoptera: twenty-eight-spotted ladybird (*Epilachna vigintioctopunctata*), cucurbit leaf beetle (*Aulacophora femoralis*), striped flea beetle (*Phyllotreta striolata*), rice leaf beetle (*Oulema oryzae*), rice curculio (*Echinocnemus squameus*), rice water weevil (*Lissorhoptrus oryzophilus*), boll weevil (*Anthonomus grandis*), azuki bean weevil (*Callosobruchus chinensis*), hunting billbug (*Sphenophorus venatus*), Japanese beetle (*Popillia japonica*), cupreous chafer (*Anomala cuprea*), corn root worms (*Diabrotica* spp.), Colorado beetle (*Leptinotarsa decemlineata*), click beetles (*Agriotes* spp.), cigarette beetle (*Lasioderma serricorne*), varied carper beetle (*Anthrenus verbasci*), red flour beetle (*Tribolium castaneum*), powder post beetle (*Lyctus brunneus*), white-spotted longicorn beetle (*Anoplophora malasiaca*), and pine shoot beetle (*Tomicus piniperda*);

Orthoptera: Asiatic locust (*Locusta migratoria*), African mole cricket (*Gryllotalpa africana*), rice grasshopper (*Oxya yezoensis*), and rice grasshopper (*Oxya japonica*);

Hymenoptera: Cabbage sawfly (*Athalia rosae*), leaf-cutting ant (*Acromyrmex* spp.), and fire ant (*Solenopsis* spp.);

Blattaria: German cockroach (*Blattella germanica*), smokybrown cockroach (*Periplaneta fuliginosa*), american cockroach (*Periplaneta americana*), brown cockroach (*Periplaneta brunnea*), and oriental cockroach (*Blatta orientalis*); and Acarina: spider mites such as two-spotted spider mite (*Tetranychus urticae*), citrus red mite (*Panonychus citri*), and *Oligonychus* spp.; eriophyid mites such as pink citrus rust mite (*Aculops pelekassi*); tarosonemid mites such as broad mite (*Polyphagotarsonemus latus*); false spider mites; peacock mites; flour mites such as mould mite (*Tyrophagus putrescentiae*); house dust mites such as American house dust mite (*Dermatophagoides farinae*), and European house dust mite (*Dermatophagoides ptrenyssnus*); and cheyletid mites such as *Cheyletus eruditus, Cheyletus malaccensis*, and *Cheyletus moorei*.

In the arthropod pest control method of the present invention (hereinafter, referred to as "the control method of the present invention" in some cases), effective amounts of the compound I and the compound A are applied to plants or growing sites of plants. By the control method of the present invention, arthropod pests can be controlled.

Effective amounts of the compound I and the compound A may be applied to arthropod pests or a place where arthropod pests inhabit or a place where arthropod pests may inhabit.

Examples of a plant which is the object of the application include foliages, seeds, bulbs and seedlings. As used herein, the bulb means a bulb, corm, rhizoma, stem tuber, root tuber and rhizophore. In the present specification, the seedling includes cutting and sugarcane stem cutting. Examples of the growing sites of plants include soil before or after planting plants.

When the application is conducted to arthropod pests of plant, plants or growing site of plants, the compound T and the compound A may be separately applied for the same period, but they are typically applied as the composition of the present invention for simplicity of the application.

Specific examples of the control method of the present invention include treatment of foliage of plants, such as foliage application; treatment to cultivation lands of plants, such as soil treatment; treatment of seeds, such as seed sterilization and seed coating; treatment of seedlings; and treatment of bulbs such as seed tuber.

Specific examples of the treatment of foliage of plants in the control method of the present invention include treatment methods of applying to surfaces of plants, such as foliage spraying and trunk spraying. The active ingredients may be applied to plants before transplantation, and examples of the treatment method of directly absorbing to the plants include a method of soaking entire plants or roots. A formulation obtained by using a solid carrier such as a mineral powder may be adhered to roots.

Examples of the soil treatment method in the control method of the present invention include spraying onto the soil, soil incorporation, and perfusion of a chemical liquid into the soil (irrigation of chemical liquid, soil injection, and dripping of chemical liquid). Examples of the place to be treated include planting hole, furrow, around a planting hole, around a furrow, entire surface of cultivation lands, the parts between the soil and the plant, area between roots, area beneath the trunk, main furrow, growing soil, seedling raising box, seedling raising tray and seedbed. Examples of the treating period include before seeding, at the time of seeding, immediately after seeding, raising period, before settled planting, at the time of settled planting, and growing period after settled planting. In the above soil treatment, active ingredients may be simultaneously applied to the plant, or a solid fertilizer such as a paste fertilizer containing active ingredients may be applied to the soil. Also active ingredients may be mixed in an irrigation liquid, and examples thereof include injecting to irrigation facilities such as irrigation tube, irrigation pipe and sprinkler, mixing into flooding liquid between furrows and mixing into culture solution. Alternatively, an irrigation liquid is mixed with active ingredients in advance and, for example, used for treatment by an appropriate irrigating method including the irrigating method mentioned above and the other methods such as sprinkling and flooding.

Examples of the method of treating seeds or bulbs in the control method of the present invention include a method of treating seeds or bulbs of plants to be protected from arthropod pests with the composition of the present invention, and specific examples thereof include a spraying treatment in which a suspension of the composition of the present invention is atomized and sprayed over surfaces of seeds or bulbs, an smearing treatment in which a wettable powder, an emulsifiable concentrate or a flowable agent of the composition of the present invention is applied to seeds or bulbs with a small amount of water added or without dilution, an immersing treatment in which seeds are immersed in a solution of the composition of the present invention for a certain period of time, a film coating treatment, and a pellet coating treatment.

Examples of the method of treating seedling in the control method of the present invention include a spraying treatment in which a dilution prepared by diluting the composition of the present invention with water so as to have a suitable concentration of the active ingredients is sprayed on the entire seedling; an immersing treatment in which a seedling is immersed in the dilution; and an application treatment in which the composition of the present invention formulated into a dust formulation is adhered on the entire seedling. Examples of the treatment of soil before or after planting seedlings include a method in which a dilution prepared by diluting the composition of the present invention with water so as to have a suitable concentration of the active ingredients is sprayed on the seedling and the soil around the seedling after planting the seedling; and a method in which the composition of the present invention formulated into a solid formulation such as a granulate or a dust formulation is sprayed on the soil around the seedling after planting the seedling.

Examples of the method of treating sugarcane in the control method of the present invention include a spraying treatment in which a dilution prepared by diluting the composition of the present invention with water so as to have a suitable concentration of the active ingredients is sprayed on the entire sugarcane stem cutting; an immersing treatment in which a sugarcane stem cutting is immersed in the dilution; and an application treatment in which the composition of the present invention formulated into a dust formulation is adhered on the entire sugarcane stem cutting. Examples of the treatment of soil before or after planting sugarcane stem cutting include a method in which a dilution prepared by diluting the composition of the present invention with water so as to have a suitable concentration of the active ingredients is sprayed on the sugarcane stem cutting and the soil around the cutting after planting the cutting and before covering it by soil; a method in which the dilution is sprayed onto the surface of soil after planting the sugarcane stem cutting and covering it by the soil; and a method in which the composition of the present invention formulated into a solid formulation such as a granulate or a dust formulation is sprayed on the sugarcane stem cutting and the soil around the cutting after planting the cutting and before covering it by soil; and a method in which the solid-formulated composition is sprayed onto the surface of soil after planting the sugarcane stem cutting and covering it by the soil.

When a plant or a growing site of plants is treated with the compound I and the compound A, the amounts of the compound I and the compound A used for the treatment may be changed depending on the kind of the plant to be treated, the kind and the occurring frequency of the arthropod pests to be controlled, formulation form, treatment period, climate condition and so on, but the amount of the active ingredients per 1,000 $m^2$ is typically within a range from 0.1 to 2,000 g, and preferably from 10 to 1000 g. In the case of soil treatment, the amount of the active ingredients per 1,000 $m^2$ is typically 0.1 to 2,000 g and preferably 1 to 1,000 g.

The emulsifiable concentrate, wettable powder, flowable agent and microcapsule are typically diluted with water, and then sprinkled for the treatment. In these cases, the total concentration of the compound I and the compound A is typically within a range from 1 to 20,000 ppm, and preferably from 10 to 1,000 ppm. The dust formulation and granule are typically used for the treatment without being diluted.

In the treatment of seeds, the amount of the active ingredients per one seed is typically within a range from 0.01 to 10 mg, and preferably 0.1 to 5 mg. The amount of the active ingredients per 100 kg of seeds is typically within a range from 1 to 300 g, and preferably from 5 to 100 g.

In the treatment of seedlings, the amount of the active ingredients per one seedling is typically within a range from 0.1 to 20 mg, and preferably from 1 to 10 mg. In the treatment of the soil before or after planting seedlings, the amount of the active ingredients per 1,000 $m^2$ is typically within a range from 0.1 to 100 g, and preferably from 1 to 50 g.

In the treatment of sugarcane, the amount of the active ingredients per one sugarcane stem cutting is typically within a range from 0.1 to 100 mg, and preferably from 1 to 50 mg. In the treatment of the soil before or after planting sugarcane stem cutting, the amount of the active ingredients per 1,000 $m^2$ is typically within a range from 0.1 to 400 g, and preferably from 1 to 200 g.

The controlling method of the present invention can be used in agricultural lands such as fields, paddy fields, lawns and orchards or in non-agricultural lands.

The present invention can be used to control arthropod pests in agricultural lands for cultivating the following "plant" and the like without adversely affecting the plant and so on.

Examples of the crops are as follows:

crops: corn, rice, wheat, barley, rye, oat, sorghum, cotton, soybean, peanut, buckwheat, beet, rapeseed, sunflower, sugarcane, tobacco, etc.;

vegetables: solanaceous vegetables (eggplant, tomato, pimento, pepper, potato, etc.), cucurbitaceous vegetables (cucumber, pumpkin, zucchini, water melon, melon, squash, etc.); cruciferous vegetables (Japanese radish, white turnip, horseradish, kohlrabi, Chinese cabbage, cabbage, leaf mustard, broccoli, cauliflower, etc.), asteraceous vegetables (burdock, crown daisy, artichoke, lettuce, etc.), liliaceous vegetables (green onion, onion, garlic, and asparagus), ammiaceous vegetables (carrot, parsley, celery, parsnip, etc.), chenopodiaceous vegetables (spinach, Swiss chard, etc.), lamiaceous vegetables (*Perilla frutescens*, mint, basil, etc.), strawberry, sweet potato, Dioscorea japonica, colocasia, etc.;

flowers;

foliage plants;

turf grasses;

fruits: pomaceous fruits (apple, pear, Japanese pear, Chinese quince, quince, etc.), stone fleshy fruits (peach, plum, nectarine, *Prunus* mume, cherry fruit, apricot, prune, etc.), citrus fruits (*Citrus unshiu*, orange, lemon, rime, grapefruit, etc.), nuts (chestnuts, walnuts, hazelnuts, almond, pistachio, cashew nuts, *macadamia* nuts, etc.), berries (blueberry, cranberry, blackberry, raspberry, etc.), grape, kaki fruit, olive, Japanese plum, banana, coffee, date palm, coconuts, etc.; and trees other than fruit trees; tea, mulberry, flowering plant, roadside trees (ash, birch, dogwood, Eucalyptus, *Ginkgo biloba*, lilac, maple, *Quercus*, poplar, Judas tree, Liquidambar formosana, plane tree, zelkova, Japanese arborvitae, fir wood, hemlock, juniper, *Pinus, Picea*, and Taxus cuspidate), etc.

The aforementioned "plants" include plants, to which tolerance to HPPD inhibitors such as isoxaflutole, ALS inhibitors such as imazethapyr and thifensulfuron-methyl, EPSP synthetase inhibitors such as glyphosate, glutamine synthetase, inhibitors such as glufosinate, acetyl-CoA carboxylase inhibitors such as sethoxydim, and herbicides such as bromoxynil, dicamba and 2,4-D has been conferred by a classical breeding method or by genetic engineering techniques.

Examples of a "plant" on which tolerance has been conferred by a classical breeding method include rape, wheat, sunflower and rice tolerant to imidazolinone ALS inhibitory herbicides such as imazethapyr, which are already commercially available under a product name of Clearfield (registered trademark). Similarly, there is a soybean on which tolerance to sulfonylurea ALS inhibitory herbicides such as thifensulfuron-methyl has been conferred by a classical breeding method, which is already commercially available under a product name of STS soybean.

Examples of a plant on which tolerance to acetyl-CoA carboxylase inhibitors such as trione oxime or aryloxy phenoxypropionic acid herbicides has been conferred by a classical breeding method include SR corn. The plant on which tolerance to acetyl-CoA carboxylase inhibitors has been conferred is described in Proceedings of the National Academy of Sciences of the United States of America (Proc. Natl. Acad. Sci. USA), vol. 87, pp. 7175-7179 (1990). A variation of acetyl-CoA carboxylase tolerant to an acetyl-CoA carboxylase inhibitor is reported in Weed Science, vol. 53, pp. 728-746 (2005) and a plant tolerant to acetyl-CoA carboxylase inhibitors can be generated by introducing a gene of such an acetyl-CoA carboxylase variation into a plant by genetically engineering technology, or by introducing a variation conferring tolerance into a plant acetyl-CoA carboxylase.

Plants tolerant to acetyl-CoA carboxylase inhibitors or ALS inhibitors or the like can be generated by introducing into the plant cell a nucleic acid for introduction of base-substitution variation represented by Chimeraplasty Technique (Gura T. 1999. Repairing the Genome's Spelling Mistakes. Science 285: 316-318) to introduce a site-directed amino acid substitution variation into an acetyl-CoA carboxylase gene or an ALS gene of the plant.

Examples of a plant on which tolerance has been conferred by genetic engineering technology include corn, soybean, cotton, rape and sugar beet which are tolerant to glyphosate, and which have been commercially available under a product name of RoundupReady (registered trademark), AgrisureGT, and so on. There are corn, soybean, cotton and rape which are made tolerant to glufosinate by genetic engineering technology, which have been commercially available under a product name of LibertyLink (registered trademark). A cotton made tolerant to bromoxynil by genetic engineering technology has been commercially available under a product name of BXN.

The aforementioned "plants" include crops genetically engineered to be able to synthesize selective toxins as known in genus *Bacillus*.

Examples of toxins expressed in such genetically, engineered crops include: insecticidal proteins derived from *Bacillus cereus* or *Bacillus popilliae*; δ-endotoxins derived from *Bacillus thuringiensis* such as Cry1Ab, Cry1Ac, Cry1F, Cry1Fa2, Cry2Ab, Cry3A, Cry3Bb1 or Cry9C; insecticidal proteins such as VIP1, VIP2, VIP3 or VIP3A; insecticidal proteins derived from nematodes; toxins generated by animals, such as scorpion toxin, spider toxin, bee toxin, or insect-specific neurotoxins; mold fungi toxins; plant lectin; agglutinin; protease inhibitors such as a trypsin inhibitor, a serine protease inhibitor, patatin, cystatin, or a papain inhibitor; ribosome-inactivating proteins (RIP) such as lycine, corn-RIP, abrin, luffin, saporin, or briodin; steroid-metabolizing enzymes such as 3-hydroxysteroid oxidase, ecdysteroid-UDP-glucosyl transferase, or cholesterol oxidase; an ecdysone inhibitor; HMG-COA reductase; ion channel inhibitors such as a sodium channel inhibitor or calcium channel inhibitor; juvenile hormone esterase; a diuretic hormone receptor; stilbene synthase; bibenzyl synthase; chitinase; and glucanase.

Toxins expressed in such genetically engineered crops also include: hybrid toxins of δ-endotoxin proteins such as Cry1Ab, Cry1Ac, Cry1F, Cry1Fa2, Cry2Ab, Cry3A, Cry3Bb1, Cry9C, Cry34Ab or Cry35Ab and insecticidal proteins such as VIP1, VIP2, VIP3 or VIP3A; partially deleted toxins; and modified toxins. Such hybrid toxins are produced from a new combination of the different domains of such proteins, by using a genetic engineering technique. As a partially deleted toxin, Cry1Ab comprising a deletion of a portion of an amino acid sequence has been known. A modified toxin is produced by substitution of one or multiple amino acids of natural toxins.

Examples of such toxins and genetically engineered plants capable of synthesizing such toxins are described in EP-A-0 374 753, WO 93/07278, WO 95/34656, EP-A-0 427 529, EP-A-451 878, WO 03/052073, and so on.

Toxins contained in such genetically engineered plants are able to confer resistance particularly to insect pests belonging to Coleoptera, Hemiptera, Diptera, Lepidoptera and Nematodes, to the plants.

Genetically engineered plants, which comprise one or multiple insecticidal pest-resistant genes and which express one or multiple toxins, have already been known, and some of such genetically engineered plants have already been on the market. Examples of such genetically engineered plants include YieldGard (registered trademark) (a corn variety for expressing Cry1Ab toxin), YieldGard Rootworm (registered trademark) (a corn variety for expressing Cry3Bb1 toxin), YieldGard Plus, (registered trademark) (a corn variety for expressing Cry1Ab and Cry3Bb1 toxins), Herculex I (registered trademark) (a corn variety for expressing Cry1Fa2 toxin and phosphinotricine N-acetyl transferase (PAT) so as to confer tolerance to glufosinate), NuCOTN33B (registered trademark) (a cotton variety for expressing Cry1Ac toxin), Bollgard I (registered trademark) (a cotton variety for expressing Cry1Ac toxin), Bollgard II (registered trademark) (a cotton variety for expressing Cry1Ac and Cry2Ab toxins), VIPCOT (registered trademark) (a cotton variety for expressing VIP toxin), NewLeaf (registered trademark) (a potato variety for expressing Cry3A toxin), NatureGard (registered trademark) Agrisure (registered trademark) GT Advantage (GA21 glyphosate-tolerant trait), Agrisure (registered trademark) CB Advantage (Bt11 corn borer (CB) trait), and Protecta (registered trademark).

The aforementioned "plants" also include crops produced by using a genetic engineering technique, which have ability to generate antipathogenic substances having selective action.

A PR protein and the like have been known as such antipathogenic substances (PRPs, EP-A-0 392 225). Such antipathogenic substances and genetically engineered crops that generate them are described in EP-A-0 392 225, WO 95/33818, EP-A-0 353 191, etc.

Examples of such antipathogenic substances expressed in genetically engineered crops include: ion channel inhibitors such as a sodium channel inhibitor or a calcium channel inhibitor, among which KP1, KP4 and KP6 toxins produced by viruses have been known; stilbene synthase; bibenzyl synthase; chitinase; glucanase; a PR protein; and antipathogenic substances generated by microorganisms, such as a peptide antibiotic, an antibiotic having a hetero ring and a protein factor associated with resistance to plant diseases (which is called a plant disease-resistant gene and is described in WO 03/000906). These antipathogenic substances and genetically engineered plants producing such substances are described in EP-A-0392225, WO95/33818, EP-A-0353191, and so on.

The "plant" mentioned above includes plants on which advantageous characters such as characters improved in oil stuff ingredients or characters having reinforced amino acid content have been conferred by genetically engineering technology. Examples thereof include VISTIVE (registered trademark) low linolenic soybean having reduced linolenic content) or high-lysine (high-oil) corn (corn with increased lysine or oil content).

Stack varieties are also included in which a plurality of advantageous characters such as the classic herbicide characters mentioned above or herbicide tolerance genes, harmful insect resistance genes, antipathogenic substance producing genes, characters improved in oil stuff ingredients or characters having reinforced amino acid content are combined.

EXAMPLES

The present invention will be described in more detail by way of Formulation Examples, Treatment Examples and Test Examples, but the present invention is not limited only to the following Examples. In the following Examples; the part represents part by weight unless otherwise specified.

Formulation Example 1

Five (5) parts of the compound I and 5 parts of the compound (1) are dissolved in a mixture of 35 parts of xylene and 35 parts of N,N-dimethylformamide, to which 14 parts of polyoxyethylene styryl phenyl ether and 6 parts of calcium dodecylbenzene sulfonate are added, and the mixture is well stirred to give an emulsifiable concentrate.

Formulation Example 2

Eight (8) parts of the compound I and 2 parts of the compound (2) are dissolved in a mixture of 35 parts of xylene and 35 parts of N,N-dimethylformamide, to which 14 parts of polyoxyethylene styryl phenyl ether and 6 parts of calcium dodecylbenzene sulfonate are added, and the mixture is well stirred to give an emulsifiable concentrate.

Formulation Example 3

Ten (10) parts of the compound I and 0.02 parts of the compound (3) are dissolved in a mixture of 35 parts of xylene and 35 parts of N,N-dimethylformamide, to which 14 parts of polyoxyethylene styryl phenyl ether and 6 parts of calcium dodecylbenzene sulfonate are added, and the mixture is well stirred to give an emulsifiable concentrate.

Formulation Example 4

Ten (10) parts of the compound I and 10 parts of the compound (1) are added to a mixture of 4 parts of sodium lauryl sulfate, 2 parts of calcium lignin sulfonate, 20 parts of a synthetic hydrated silicon oxide fine powder and 54 parts of diatomaceous earth, and the mixture is stirred with a mixer to give a wettable powder.

Formulation Example 5

Twenty (20) parts of the compound I and 2 parts of the compound (2) are added to a mixture of 4 parts of sodium lauryl sulfate, 2 parts of calcium lignin sulfonate, 20 parts of a synthetic hydrated silicon oxide fine powder and 54 parts of diatomaceous earth, and the mixture is stirred with a mixer to give a wettable powder.

Formulation Example 6

Ten (10) parts of the compound I and 10 parts of the compound (3) are added to a mixture of 4 parts of sodium lauryl sulfate, 2 parts of calcium lignin sulfonate, 20 parts of a synthetic hydrated silicon oxide fine powder and 54 parts, of diatomaceous earth, and the mixture is stirred with a mixer to give a wettable powder.

Formulation Example 7

To 1 part of the compound I and 1 part of the compound (1), 1 part of a synthetic hydrated silicon oxide fine powder, 2 parts of calcium lignin sulfonate, 30 parts of bentonite and 65 parts of kaolin clay are added, followed by well mixing with stirring. Then, a suitable amount of water is added to the mixture, which is further stirred, granulated with a granulator and then airdried to give a granule.

Formulation Example 8

To 1 part of the compound I and 1 part of the compound (2), 1 part of a synthetic hydrated silicon oxide fine powder, 2 parts of calcium lignin sulfonate, 30 parts of bentonite and 65 parts of kaolin clay are added, followed by well mixing with stirring. Then, a suitable amount of water is added to the mixture, which is further stirred, granulated with a granulator and then air-dried to give a granule.

Formulation Example 9

To 2 part of the compound I and 0.2 parts of the compound (3), 1 part of a synthetic hydrated silicon oxide fine powder, 2 parts of calcium lignin sulfonate, 30 parts of bentonite and 65 parts of kaolin clay are added, followed by well mixing with stirring. Then, a suitable amount of water is added to the mixture, which is further stirred, granulated with a granulator and then air-dried to give a granule.

Formulation Example 10

One (1) part of the compound I and 1 part of the compound (1) are dissolved in a proper amount of acetone, to which 5 parts of a synthetic hydrated silicon oxide fine powder, 0.3 parts of PAP and 92.7 parts of Fubasami clay are added, followed by well mixing with stirring. The removal of acetone by evaporation gives a dust formulation.

Formulation Example 11

One (1) part of the compound I and 1 part of the compound (2) are dissolved in a proper amount of acetone, to which 5 parts of a synthetic hydrated silicon oxide fine powder, 0.3 parts of PAP and 92.7 parts of Fubasami clay are added, followed by well mixing with stirring. The removal of acetone by evaporation gives a dust formulation.

Formulation Example 12

One (1) part of the compound I and 1 part of the compound (3) are dissolved in a proper amount of acetone, to which 5 parts of a synthetic hydrated silicon oxide fine powder, 0.3 parts of PAP and 92.7 parts of Fubasami clay are added, followed by well mixing with stirring. The removal of acetone by evaporation gives a dust formulation.

Formulation Example 13

Ten (10) parts of the compound I, 10 parts of the compound (1), 35 parts of white carbon containing 50 parts of a polyoxyethylene alkyl ether sulfate ammonium salt, and 45 parts of water are mixed and the mixture is finely ground by a wet grinding method to give a flowable formulation.

Formulation Example 14

Ten (10) parts of the compound I, 10 parts of the compound (2), 35 parts of white carbon containing 50 parts of a polyoxyethylene alkyl ether sulfate ammonium salt, and 45 parts of water are mixed and the mixture is finely ground by a wet grinding method to give a flowable formulation.

Formulation Example 15

Ten (10) parts of the compound I, 10 parts of the compound (3), 35 parts of white carbon containing 50 parts of a polyoxyethylene alkyl ether sulfate ammonium salt, and 45 parts of water are mixed and the mixture is finely ground by a wet grinding method to give a flowable formulation.

Formulation Example 16

One (1) part of the compound I and 0.1 part of the compound (1) are dissolved in 5 parts of xylene and 5 parts of trichloroethane, followed by mixing with 88.9 parts of a deodorized kerosine to give an oil agent.

Formulation Example 17

Two (2) parts of the compound I and 0.1 part of, the compound (2) are dissolved in 5 parts of xylene and 5 parts of trichloroethane, followed by mixing with 88.9 parts of a deodorized kerosine to give an oil agent.

Formulation Example 18

One (1) part of the compound I and 1 part of the compound (3) are dissolved in 5 parts of xylene and 5 parts of trichloroethane, followed by mixing with 88.9 parts of a deodorized kerosine to give an oil agent.

Treatment Example 1

To 20 parts of the compound I and 5 parts of the compound (1), 65 parts of cyclohexanone, 5 parts of NINATE 401-A and 5 parts of BLAUNON BR-450 are added, followed by well mixing with stirring to give an emulsifiable concentrate.

Then, the emulsifiable concentrate is diluted with water by 1,000 times to prepare a dilution, and rice seeds are soaked in the dilution for 24 hours until active ingredients are absorbed into the rice seeds to give treated seeds.

Treatment Example 2

To 12.5 parts of the compound I and 12.5 parts of the compound (2), 65 parts of cyclohexanone, 5 parts of NINATE 401-A and 5 parts of BLAUNON BR-450 are added, followed by well mixing with stirring to give an emulsifiable concentrate.

Then, the emulsifiable concentrate is diluted with water by 1,000 times to prepare a dilution, and rice seeds are soaked in the dilution for 24 hours until active ingredients are absorbed into the rice seeds to give treated seeds.

Treatment Example 3

To 12.5 parts of the compound I and 12.5 parts of the compound (3), 65 parts of cyclohexanone, 5 parts of NINATE 401-A and 5 parts of BLAUNON BR-450 are added, followed by well mixing with stirring to give an emulsifiable concentrate.

Then, the emulsifiable concentrate is diluted with water by 1,000 times to prepare a dilution, and rice seeds are soaked in the dilution for 24 hours until active ingredients are absorbed into the rice seeds to give treated seeds.

Treatment Example 4

Well mixed are 20 parts of the compound I and 2 parts of the compound (1), 25 parts of clay for the formulation, 25 parts of polyvinyl alcohol containing 50 parts of SOLGEN TW-20, and 25 parts of water with stirring to give a material for forming pellets.

Then, cabbage seeds are embedded in the center of 20 mg of the material for forming pellets, followed by forming into spheres and further drying to give treated seeds.

Treatment Example 5

Well mixed are 15 parts of the compound I and 5 parts of the compound (2), 25 parts of clay for the formulation, 25 parts of polyvinyl alcohol containing 50 parts of SOLGEN TW-20, and 25 parts of water with stirring to give a material for forming pellets.

Then, cabbage seeds are embedded in the center of 20 mg of the material for forming pellets, followed by forming into spheres and further drying to give treated seeds.

Treatment Example 6

Well mixed are 12.5 parts of the compound I and 12.5 parts of the compound (3), 25 parts of clay for the formulation, 25 parts of polyvinyl alcohol containing 50 parts of SOLGEN TW-20, and 25 parts of water with stirring to give a material for forming pellets.

Then, cabbage seeds are embedded in the center of 20 mg of the material for forming pellets, followed by forming into spheres and further drying to give treated seeds.

Treatment Example 7

Mixed are 15 parts of the compound I and 5 parts of the compound (1), 20 parts of white carbon containing 50% (weight) of a polyoxyethylene alkyl ether sulfate ammonium salt, and 55 parts of water, and finely ground by a wet grinding method to give a flowable formulation.

Cotton seeds are put in a stainless steel pot (having a volume of about 1,200 mL) equipped with a lifting blade for lifting seeds when the pot is rotated, and then the pot is inclined at an angle of about 45 degrees and mechanically rotated so that satisfactory mixing and tumbling granulating effect can be obtained in the pot.

The flowable formulation is diluted with water by 100 times and a hand sprayer is turned toward the inside of the pot, and then the dilution is directly sprayed to the center of a tumbling granulating layer of cotton seeds. Furthermore, the sprayer is stopped and low-pressure air is sprayed to seeds, and then the seed coating is immediately dried.

Thereafter, spraying using a hand sprayer is restarted. This spraying and drying cycle is repeated until a predetermined amount of a fluid suspension is applied to seeds, to give treated seeds.

Treatment Example 8

Mixed are 12.5 parts of the compound I and 12.5 parts of the compound (2), 20 parts of white carbon containing 50% (weight) of a polyoxyethylene alkyl ether sulfate ammonium salt, and 55 parts of water, and finely ground by a wet grinding method to give a flowable formulation.

Cotton seeds are put in a stainless steel pot (having a volume of about 1,200 mL) equipped with a lifting blade for lifting seeds when the pot is rotated, and then the pot is inclined at an angle of about 45 degrees and mechanically rotated so that satisfactory mixing and tumbling granulating effect can be obtained in the pot.

The flowable formulation is diluted with water by 100 times and a hand sprayer is turned toward the inside of the pot, and then the dilution is directly sprayed to the center of a tumbling granulating layer of cotton seeds. Furthermore, the sprayer is stopped and low-pressure air is sprayed to seeds, and then the seed coating is immediately dried.

Thereafter, spraying using a hand sprayer is restarted. This spraying and drying cycle is repeated until a predetermined amount of a fluid suspension is applied to seeds, to give treated seeds.

Treatment Example 9

Mixed are 20 parts of the compound I and 10 parts of the compound (3), 20 parts of white carbon containing 50% (weight) of a polyoxyethylene alkyl ether sulfate ammonium salt, and 55 parts of water, and finely ground by a wet grinding method to give a flowable formulation.

Cotton seeds are put in a stainless steel pot (having a volume of about 1,200 mL) equipped with a lifting blade for lifting seeds when the pot is rotated, and then the pot is inclined at an angle of about 45 degrees and mechanically rotated so that satisfactory mixing and tumbling granulating effect can be obtained in the pot.

The flowable formulation is diluted with water by 100 times and a hand sprayer is turned toward the inside of the pot, and then the dilution is directly sprayed to the center of a tumbling granulating layer of cotton seeds. Furthermore, the sprayer is stopped and low-pressure air is sprayed to seeds, and then the seed coating is immediately dried.

Thereafter, spraying using a hand sprayer is restarted. This spraying and drying cycle is repeated until a predetermined amount of a fluid suspension is applied to seeds, to give treated seeds.

Treatment Example 10

To 10 parts of the compound I and 1 part of the compound (1), 65 parts of cyclohexanone, 5 parts of NINATE 401-A and 5 parts of BLAUNON BR-450 are added, followed by well mixing with stirring to give an emulsifiable concentrate.

Then, the emulsifiable concentrate is diluted with water by 1,000 times to prepare a dilution, and the dilution is sprayed onto a sugarcane stem cutting.

Treatment Example 11

To 10 parts of the compound I and 1 part of the compound (2), 65 parts of cyclohexanone, 5 parts of NINATE 401-A and 5 parts of BLAUNON BR-450 are added, followed by well mixing with stirring to give an emulsifiable concentrate.

Then, the emulsifiable concentrate is diluted with water by 1,000 times to prepare a dilution, and the dilution is sprayed onto a sugarcane stem cutting.

Treatment Example 12

To 10 parts of the compound I and 1 part of the compound (3), 65 parts of cyclohexanone, 5 parts of NINATE 401-A and 5 parts of BLAUNON BR-450 are added, followed by well mixing with stirring to give an emulsifiable concentrate.

Then, the emulsifiable concentrate is diluted with water by 1,000 times to prepare a dilution, and the dilution is sprayed onto a sugarcane stem cutting.

Test Example 1

The compound I was dissolved in water to prepare an aqueous solution having a prescribed concentration. Also, the compound (1) (Coragen (registered trademark), product of DuPont) was diluted with water to prepare a chemical solution of the compound. These solutions were appropriately mixed to prepare a test mixed chemical solution having a prescribed concentration of the compound I and the compound (1).

A 90 mL plastic cup was filled with cultivation soil and 15 rice seeds were sown.

Two weeks after seedlings emerged, the foot of rice seedlings were treated with the test mixed chemical solution (5 mL/plastic cup). After 2 days, 30 of first-instar larvae of *Pseudaletia separata* were released per plastic cup. After 3 days, the number of surviving larvae was counted and the control rate was calculated using the equation A.

For comparison, tests were conducted in the same manner using a test aqueous solution having a prescribed concentration of the compound I, prepared by diluting an aqueous solution of the compound I with water, and a test aqueous solution having a prescribed concentration of the compound (1), prepared by diluting an aqueous solution of the compound (1) with water.

The results are shown in Table 1.

In a treatment with a mixture of the compound I and the compound (1), an effect better than that in the case of treatment with the compound I or the compound (1) singly was observed.

$$\text{Control rate}=100\times(1-[(Ts/30)/(Cs/30)]) \qquad \text{"Equation A"}$$

Ts and Cs represent the number of surviving larvae in a treated group and that in a non-treated group, respectively. Provided that, when the control rate is less than 0 (Ts>Cs), it is indicated by 0.

TABLE 2

| Test compound(s) | Active ingredient concentration (ppm) | Control rate (%) |
|---|---|---|
| Compound I + | 10 + 1.0 | 87 |
| Compound (1) | 10 + 3.0 | 100 |
|  | 30 + 1.0 | 87 |
|  | 30 + 3.0 | 100 |
|  | 100 + 1.0 | 100 |
|  | 100 + 3.0 | 100 |
| Compound I | 10 | 0 |
|  | 30 | 0 |
|  | 100 | 0 |
| Compound (1) | 1.0 | 78 |
|  | 3.0 | 87 |

Test Example 2

The compound I was dissolved in water to prepare an aqueous solution having a prescribed concentration. Also, the compound (2) was dissolved in a mixed solution (44:1) of acetone and Tween 20, followed by dilution with water to prepare a chemical solution. These solutions were appropriately mixed to prepare a test mixed chemical solution having a prescribed concentration of the compound I and the compound (2).

A 90 mL plastic cup was filled with cultivation soil and 15 rice seeds were sown.

Two weeks after seedlings emerged, the foot of rice seedlings were treated with the test mixed chemical solution (5 mL/plastic cup). After 2 days, 30 of first-instar larvae of Pseudaletia separata were released per plastic cup. After 3 days, the number of surviving larvae was counted and the control rate was calculated using the equation A in the same manner as in Test Example 1.

For comparison, tests were conducted in the same manner using a test aqueous solution having a prescribed concentration of the compound I, prepared by diluting an aqueous solution of the compound I with water, and a test chemical solution having a prescribed concentration of the compound (2), prepared by dissolving the compound (2) in a mixed solution (1:9) of acetone and Tween 20, followed by dilution with water.

The results are shown in Table 3.

In a treatment with a mixture of the compound I and the compound (2), an effect better than that in the case of a treatment with the compound I or the compound (2) singly was observed.

TABLE 3

| Test compound(s) | Active ingredient concentration (ppm) | Control rate (%) |
|---|---|---|
| Compound I + Compound (2) | 30 + 1.0 | 82 |
|  | 100 + 1.0 | 82 |
| Compound I | 30 | 0 |
|  | 100 | 0 |
| Compound (2) | 1.0 | 59 |

The compound (2) used in Test Example 2 was produced according to the following method.

2.22 g of 2-[3-bromo-1-(3-chloro-2-pyridinyl)-1H-pyrazol-5-yl]-6-cyano-8-methyl-4H-3,1-benzoxazin-4-one and 20 mL of tetrahydrofuran were mixed, followed by cooling to −40° C. To the mixture, 3 mL of a tetrahydrofuran solution of 2 M methylamine was added dropwise, followed by heating to −20° C. and further stirring at −20° C. for 10 minutes. 20 mL of 10% citric acid and 10 mL of water were poured into the reaction mixture, followed by stirring at 0° C. for 10 minutes. The precipitated crystal was filtered and the filter cake was washed with 30 mL of water and 15 mL of acetonitrile to obtain the compound (2).

The Compound (2)

$^1$H-NMR (DMSO-$d_6$) δ(ppm): 2.21 (3H, s), 2.64-2.71 (3H, m), 7.41 (1H, s), 7.61 (1H, dd, J=8 Hz, 5 Hz), 7.75-7.78 (1H, m), 7.88 (1H, brs), 8.17 (1H, dd, J=8 Hz, 2 Hz), 8.34-8.43 (1H, m), 8.50 (1H, dd, J=5 Hz, 2 Hz), 10.52 (1H, s)

Test Example 3

The compound I was dissolved in water to prepare an aqueous solution having a prescribed concentration. Also, the compound (3) was dissolved in a mixed solution (44:1) of acetone and Tween 20, followed by dilution with water to prepare a chemical solution. These solutions were appropriately mixed to prepare a test mixed chemical solution having a prescribed concentration of the compound I and the compound (3).

A 90 mL plastic cup, was filled with cultivation soil and 15 rice seeds were sown.

Two weeks after seedlings emerged, the rice seedlings were treated with the test mixed chemical solution (20 mL/plastic cup). After air dying, 30 of first-instar larvae of Pseudaletia separata were released per plastic cup. After 3 days, the number of surviving larvae was counted and the control rate was calculated using the equation A in the same manner as in Test Example 1 and Test Example 2.

For comparison, tests were conducted in the same manner using a test aqueous solution having a prescribed concentration of the compound I, prepared by diluting an aqueous solution of the compound I with water, and a test chemical solution having a prescribed concentration of the compound (3), prepared by dissolving the compound (3) in a mixed solution (1:9) of acetone and Tween 20, followed by dilution with water.

The results are shown in Table 4.

In a treatment with a mixture of the compound I and the compound (3), an effect better than that in the case of a treatment with the compound I or the compound (3) singly was observed.

TABLE 4

| Test compound(s) | Active ingredient concentration (ppm) | Control rate (%) |
|---|---|---|
| Compound I + Compound (3) | 10 + 0.3 | 71 |
|  | 30 + 0.3 | 79 |
|  | 100 + 0.3 | 79 |
| Compound I | 10 | 0 |
|  | 30 | 0 |
|  | 100 | 0 |
| Compound (3) | 0.3 | 58 |

The compound (3) used in Test Example 3 was produced according to the following method.

To a mixed solution of 0.6 g of α-methyl-cyclopropylmethylamine hydrochloride and 40 mL of tetrahydrofuran, 1 g of triethylamine was gradually added dropwise under ice cooling, followed by stirring at room temperature for 1 hour. Next, a mixed solution of 0.85 g of 2-[3-bromo-1-(3-chloro-2-pyridinyl)-1H-pyrazol-5-yl]-6-chloro-8-bromo-4H-3,1-benzoxazin-4-one and 10 mL of tetrahydrofuran was gradually added dropwise. After completion of the dropwise addition, the mixed solution was reacted under reflux for 4 hours. After completion of the reaction, the solvent was distilled off under reduced pressure and extraction was carried out by adding ethyl acetate and water to the residue. The organic layer was washed in turn with water and saturated brine, and then dried over anhydrous magnesium sulfate added. The solvent was distilled off under reduced pressure and the residue was purified by silica gel column chromatography (eluant: n-hexane/ethyl acetate=1/2) to obtain the compound (3).

INDUSTRIAL APPLICABILITY

According to the present invention, an arthropod pest control composition having excellent control efficacy and a method effective for controlling arthropod pests can be provided.

The invention claimed is:

1. An arthropod pests control composition comprising, as active ingredients, 4-oxo-4-[(2-phenylethyl)amino]-butyric acid and a compound represented by formula (A):

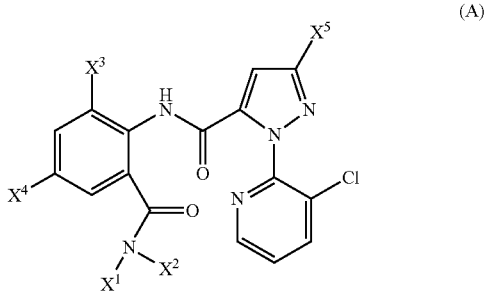

wherein $X^1$ represents a C1-C3 alkyl group or a hydrogen atom, $X^2$ represents a methyl group or —CH(CH$_3$)-cycPr, $X^3$ represents a methyl group or a halogen atom, $X^4$ represents a methyl group, a cyano group or a halogen atom, and $X^5$ represents a trifluoromethyl group or a halogen atom.

2. The arthropod pests control composition according to claim 1, wherein a weight ratio of 4-oxo-4-[(2-phenylethyl)amino]-butyric acid to the compound represented by the formula (A) is in the range of 0.1:1 to 500:1.

3. A seed treatment agent comprising, as active ingredients, 4-oxo-4-[(2-phenylethyl)amino]-butyric acid and a compound represented by formula (A) of claim 1.

4. A plant seed treated with effective amounts of 4-oxo-4-[(2-phenylethyl)amino]-butyric acid and a compound represented by formula (A) of claim 1.

5. A method of controlling arthropod pests which comprises applying effective amounts of 4-oxo-4-[(2-phenylethyl)amino]-butyric acid and a compound represented by formula (A) of claim 1 to a plant or growing site of plant.

6. The method of controlling arthropod pests according to claim 5, wherein the plant is a seed or seedling.

7. The method of controlling arthropod pests according to claim 5, wherein the growing site of plant is soil before or after planting the plant on it.

* * * * *